United States Patent [19]

Graham, Jr. et al.

[11] Patent Number: 4,743,542
[45] Date of Patent: May 10, 1988

[54] METHOD FOR FORESTALLING THE HOOK EFFECT IN A MULTI-LIGAND IMMUNOASSAY SYSTEM

[75] Inventors: Henry A. Graham, Jr., Annandale; Peter Lisi, Somerville, both of N.J.

[73] Assignee: Ortho Diagnostic, Raritan, N.J.

[21] Appl. No.: 722,566

[22] Filed: Apr. 11, 1985

[51] Int. Cl.$^4$ .................. G01N 33/546; G01N 33/577
[52] U.S. Cl. ........................................ 435/7; 436/501; 436/533; 436/534; 436/548; 436/818
[58] Field of Search ............... 435/4, 7; 436/518, 528, 436/531, 534, 817, 501, 533, 548, 818

[56] References Cited

U.S. PATENT DOCUMENTS

| | | | |
|---|---|---|---|
| 4,230,797 | 10/1980 | Boguslaski et al. | 435/7 |
| 4,248,965 | 2/1981 | Mochida et al. | 435/7 |
| 4,595,661 | 6/1986 | Cragle et al. | 436/534 |

FOREIGN PATENT DOCUMENTS

WO8502258  5/1985  PCT Int'l Appl. ............ 33/53

*Primary Examiner*—Sidney Marantz
*Attorney, Agent, or Firm*—Richard J. Grochala; Mark A. Hofer

[57] ABSTRACT

A method is provided for substantially increasing the dynamic range of an immunoassay and forestalling the hook effect observed with very large ligand concentrations in aqueous samples. The method comprises the addition of ligand binding partners which do not have labels associated therewith to compete with labeled ligand binding partners thereby effectively eliminating the presence of the excess ligand in the sample solution. The conversant method for ligand binding partner immunoassays is also provided.

9 Claims, 1 Drawing Sheet

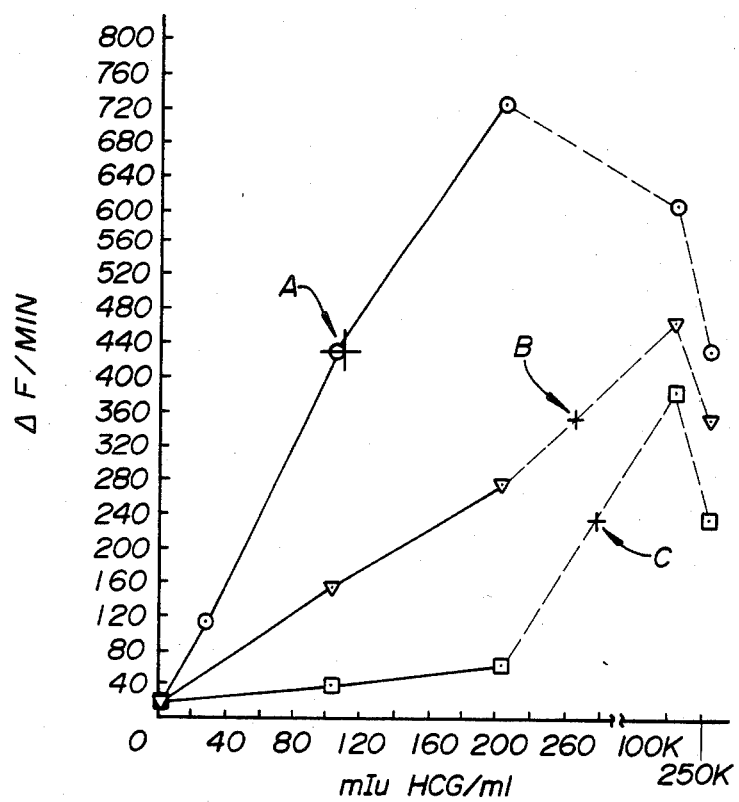

METHOD FOR FORESTALLING THE HOOK EFFECT IN A MULTI-LIGAND IMMUNOASSAY SYSTEM

FIELD OF THE INVENTION

This invention is related to immunoassays generally, and more particularly is useful in immunoassay systems for the detection of a variety of ligands utilizing a standard procedure and a minimum of ligand specific reagents, all of which are soluble, and a set of common reagents including an isotactic surface means.

BACKGROUND OF THE INVENTION

The development of immunological techniques for the detection of disease associated materials such as antigens by their immunological reactivity with substances specific therefor, typically called antibodies, has been hindered by a number of technical problems. In particular, one of these problems is the so-called hook effect which introduces significant nonlinearity in assay sensitivity at high antigen concentrations. An additional undesireable characteristic is the accompanying limit in dynamic range.

The hook effect is perhaps most easily understood in relation to the standard sandwich assay for the detection of a ligand. Typically, such an assay employs a first ligand binding partner, insolubilized such as by attachment to the wall of a microtitration tray well, and a second ligand binding partner having associated therewith a detectable label. Mixing together an aqueous body fluid sample suspected of containing the ligand to be detected, along with the aqueous labeled second binding partner and the immobilized first binding partner under suitable conditions, e.g. incubation at 37° C. for sufficient time, permits the formation of a sandwich complex wherein the first binding partner specifically reacts with the ligand to be detected, this results in its immobilization onto the wall of the micotitration well. Similarly, the second binding partner reacts with the ligand and thus the label associated therewith also becomes immobilized. Soluble components remaining in solution which have not reacted are thereafter removed and the amount of label in either the soluble or insoluble phase detected. The amount of label detected can be related to the quantity of ligand present in the fluid sample.

Typically, the immobilized first ligand binding partner is supplied in excess in order to ensure that sufficient binding sites are available for the retention of all possible ligands within the sample. The quantity of second ligand binding partner supplied in the reagent will, of course, be fixed and is generally set at a concentration level well below that which would result in nonspecific absorption to the insoluble phase, but still sufficiently high to thereby provide enough label for attachment to a reasonably high, clinically significant ligand concentration.

Unfortunately, however, patient samples are often not so accommodating and may present a far wider range of concentrations of ligands requiring a greater dynamic range of sensitivity response than such an assay has heretofore afforded. In particular, the hook effect becomes significant with very large ligand concentrations. In such situations, there is so much ligand present in the sample that all available combining sites on the immobilized first ligand binding partner as well as those available on the second labeled ligand binding partner are filled with the available ligand. Indeed, there may still be additional unattached ligands available. As a result of the plethora of ligands available fewer sandwich complexes are being formed since only some of the first and second ligand binding partners will be attached to the same ligand. Consequently, an increasing ligand concentration results in a proportional increase in immobilized label until the ligand concentration becomes so great that fewer sandwich complexes are formed whereupon the curve rapidly drops off giving a false, lower concentration of ligand. This is the hook effect.

It will be readily appreciated that the predominant danger introduced by the hook effect is the erroneous indication of far smaller ligand concentrations than are actually present in the sample. Conventional immunoassay methods have attempted to address the hook-effect problem by supplying greater numbers of both the labeled and immobilized ligand binding partners in order to accommodate greater ligand concentrations. This approach, however, disadvantageously results in greater economic costs and is further constrained by present technology which limits the amount of ligand binding partners which may be immobilized per unit area on a solid phase. Such increased concentrations may also be at the expense of sensitivity since increasing the numbers of binding partners and the area available for attachment of binding partners can result in greater difficulty in locating and forming sandwich complexes with the few ligands that may be present in a sample having a very low ligand concentration.

It is one aspect of the present invention to reduce the hook effect in clinically useful ligand concentration ranges without increasing the immobilized or labeled ligand binding partners.

The other conventional alternative for addressing the hook-effect practiced to date is serial dilution of samples having ligand concentrations at some preset level in order to bring the sample within the dynamic range which may be handled by the assay system. This disadvantageously results in additional steps; indeed a complete duplication of the assay for those samples having high ligand concentrations.

It is yet another aspect of the present invention to reduce the number of occasions when dilution of patient samples is required by extending the dynamic range of sensitivity.

Related copending, commonly assigned, U.S. application Ser. No. 722,110 entitled "Immunoassay Methods for Single and Multiple Epitopic Ligands Utilizing Isotactic Surfaces" and fully incorporated herein by reference describes an immunoassay system for the detection of a variety of ligands utilizing a standard procedure and standard volumes of samples and reactants.

It is still yet another aspect of the present invention to provide a method for reducing the hook-effect whereby the volumes of the reactants in the immunoassay system described in U.S. Ser. No. 722,110 may be standardized and the need to perform serial dilutions is reduced due to the extension of sensitivity dynamic range.

BRIEF SUMMARY OF THE INVENTION

In accordance with the aspects and principles of the instant invention, there is provided a method for reducing the hook effect in immunoassays which is especially useful for immunoassay systems for the detection of ligands wherein the order of reactions, volumes of reactants, and number of wash steps are kept constant between ligand assays. The normal immunoassay reactants will preferably include a haptenated ligand binding partner specific for the ligand to be detected and an insoluble, isotactic surface means for immobilizing said haptenated first binding partner. The reactants will preferably further include a reaction component having an enzyme label associated therewith and which becomes associated with said first binding partner in accordance with the presence or absence of the ligand to be detected. The method of the instant invention comprises adjustment of the reactants by addition to the aforedescribed reactants, ligand binding partner without associated hapten or, reaction component without associated enzyme label, or a combination thereof.

BRIEF DESCRIPTION OF THE DRAWINGS

Further understanding of the principles of the present invention may be had by reference to the FIGURE showing the presence of the hook-effect in a sandwich assay and reduction of the hook effect with an accompanying increase in dynamic range of sensitivity as a result of the present invention.

DETAILED DESCRIPTION OF THE DRAWING AND BEST MODE

The instant invention is particularly useful in conjunction with the immunoassay system described in commonly assigned copending U.S. application Ser. Nos. 722,110 and 722,244 entitled "Clinical Laboratory Management System" both of which are fully incorporated herein by reference.

The FIGURE demonstrates the principles of the instant invention. The uppermost curve shows the results from an assay for HCG utilizing the immunoassay procedure as described in U.S. Ser. No. 722,244. In brief, that procedure provides for mixture of 25 $\mu$l of a standard of HCG (50 $\mu$l used for the example shown merely in order to double the signals received and clearly demonstrate the effectiveness and utility of the present invention) with 50 $\mu$l of HCG specific reagent comprising a first HCG specific binding partner (monoclonal antibody) labeled with a hapten (fluorescein isothiocyanate) and a second HCG binding partner (monoclonal antibody) labeled with an enzyme ($\beta$-galactosidase). The standard and HCG specific reagents are mixed along with 100 $\mu$l of an isotactic surface means (latex microsphere coated with anti-fluorescein monoclonal antibody) for specifically immobilizing hapten associated materials and thus in turn, ligands and second ligand binding partners. The reactants are incubated and unreacted components removed by suction through a microtitration tray having a filter membrane at the bottom of the wells. The reactants are preferably washed to remove nonspecifically reacted materials and 100 $\mu$l of enzyme substrate ($1 \times 10^{-4}$ M 4-methylumbelliferol-Beta-D- Galactoside) added and the development of fluorescence product (4-methylumbelliferol) monitored. As can be readily seen, a relatively small dynamic range results (e.g. 0-100 mIu HCG/ml) along with a pronounced hook effect giving rise to errors in the event mili milli international units of HCG per ml of sample exceeds about 100. This level, point A, obtains due to the identical level in the hook region from the very high concentration levels (250K mIu/ml) to be tested. Thus, anything giving rise to a reading in excess of 100 mIu/ml will require dilution.

The present invention provides for the extension of this dynamic range thereby allowing for more clinically useful ranges of HCG (or other ligands) to be detected and to thereby eliminate or substantially reduce the deleterious hook effect. The instant invention may be advantageously accomplished by either of two ways. One may add additional unhaptenated binding partner (anti-HCG), or preferably, nonenzyme labeled binding partner (anti-HCG) to the previously described reactant components. It is not believed that choice of one over the other is significant. Alternately, a combination of the "cold" ligand binding partners can be added although this route is believed to be more difficult to control for deriving the desired dynamic ranges.

EXAMPLE 1

To the reactants described previously, 400 nanograms per ml of nonenzyme labeled anti-HCG were added per well and the assay performed as previously described. As can be readily seen from the middle curve, the dynamic range has been increased to approximately 242 mIu/ml (point B) and the hook effect delayed to substantially double the concentration of HCG observed in the unadjusted control.

EXAMPLE 2

2000 nanograms per ml of anti-HCG without enzyme label were added to the reactants set forth in the assay first described and the assay performed as aforementioned. As can now be readily appreciated, the dynamic range has been increased still further to approximately 255 mIu/ml at point C and the hook effect forestalled to still higher concentrations of HCG before serial dilutions are required.

As may be readily appreciated, one skilled in the art would wish to adjust the addition of nonlabeled reactants in order to optimize the dynamic range while still maintaining an adequate level of sensitivity. Sensitivity is typically limited by the purity and activity of the labels employed and the capability of the instrument used to colorimetrically or fluorometrically measure the production of enzymatic product. Clearly, one would wish to avoid the extreme of adding a great excess of unlabeled anti-HCG to very few labeled anti-HCG in order to derive an assay having a tremendous dynamic range but also possessing such a small delta fluorescence per minute (e.g. sensitivity) that no instrument made would be capable of detecting the presence of such low concentrations of enzymatic label. Those skilled in this art are conversant with such trade-offs and will realize the importance of maintaining the necessary level of sensitivity while obtaining the benefits of this invention for extending the dynamic range with the instant invention.

Further, one skilled in the art will readily appreciate that the principles of the instant invention are not limited to the preferred immunoassay system described in U.S. Ser. No. 722,110, but indeed, may be utilized in virtually all immunoassay techniques.

What is claimed is:

1. In an immunoassay for the detection of a ligand wherein a first ligand binding partner specific for the ligand to be detected is immobilized by attachment to an insoluble surface and is reacted with a second ligand binding partner specific for the ligand to be detected, said second ligand binding partner having a detectable label and forming a sandwich complex with said first binding partner in accordance with the presence or absence of the ligand to be detected, the improvement comprising:
  (a) providing a haptenated first ligand binding partner and an insoluble isotactic surface means capable of reacting with and immobilizing said haptenated first binding partner; and
  (b) adding to said reactants either additional non-haptenated first ligand binding partner or non-labeled second ligand binding partner or a combination thereof, so as to bind excess ligand to be detected and permit formation of an increased number of sandwich complexes thereby increasing the dynamic range of detection sensitivity to said immunoassay.

2. The immunoassay of claim 1, wherein the first ligand binding partner is haptenated with a fluorescent molecule.

3. The immunoassay of claim 1, wherein the isotactic surface means is a latex bead coated with anti-hapten monoclonal antibody.

4. In an immunoassay for the detection of a ligand wherein a first ligand binding partner associated with an insoluble surface and specific for the ligand to be detected is reacted with a second ligand binding partner specific for the ligand to be detected, said second ligand binding partner having a detectable label and forming a sandwich complex with said first binding partner in accordance with the presence or absence of the ligand to be detected, the improvement comprising:
  adding to said reactants either additional first ligand binding partner not associated with said insoluble surface or non-labeled second ligand binding partner or a combination thereof, so as to bind excess ligand to be detected and permit formation of an increased number of sandwich complexes thereby increasing the dynamic range of detection sensitivity of said immunoassay.

5. The immunoassay of claim 1 or claim 4, wherein the ligand is an antigen.

6. The immunoassay of claim 1 or claim 4, wherein the first ligand binding partner is a monoclonal antibody.

7. The immunoassay of claim 1 or claim 4, wherein the second ligand binding partner is a monoclonal antibody.

8. The immunoassay of claim 1 or claim 4, wherein the detectable label is a fluorescent or enzyme label.

9. The immunoassay of claim 1 or claim 4, wherein the dynamic range of detection sensitivity is increased by a factor of about 2.5.

* * * * *